(12) United States Patent
Tenore

(10) Patent No.: US 8,101,707 B2
(45) Date of Patent: Jan. 24, 2012

(54) PROCESS FOR THE DIRECT MANUFACTURE OF POLYGLYCEROL POLYRICINOLEATE

(75) Inventor: Richard R. Tenore, Sparta, NJ (US)

(73) Assignee: Stepan Company, Northfield, IL (US)

( * ) Notice: Subject to any disclaimer, the term of this patent is extended or adjusted under 35 U.S.C. 154(b) by 133 days.

(21) Appl. No.: 11/997,497

(22) PCT Filed: Aug. 17, 2006

(86) PCT No.: PCT/US2006/032237
§ 371 (c)(1),
(2), (4) Date: Jan. 31, 2008

(87) PCT Pub. No.: WO2007/027447
PCT Pub. Date: Mar. 8, 2007

(65) Prior Publication Data
US 2008/0233059 A1   Sep. 25, 2008

Related U.S. Application Data

(60) Provisional application No. 60/712,376, filed on Aug. 30, 2005.

(51) Int. Cl.
*C08G 65/332* (2006.01)
(52) U.S. Cl. ....................... 528/361; 528/275
(58) Field of Classification Search .................. 528/275, 528/361
See application file for complete search history.

(56) References Cited

U.S. PATENT DOCUMENTS

| | | | | |
|---|---|---|---|---|
| 5,585,506 A | * | 12/1996 | Harvey et al. | 554/173 |
| 6,042,815 A | * | 3/2000 | Kellner et al. | 424/63 |
| 2002/0058781 A1 | * | 5/2002 | Lemke | 528/425 |
| 2003/0065027 A1 | * | 4/2003 | Brock et al. | 514/547 |

FOREIGN PATENT DOCUMENTS

| | | | |
|---|---|---|---|
| GB | 2073232 A | * | 10/1981 |
| JP | 05049398 A | * | 3/1993 |
| JP | 06220484 A | * | 8/1994 |

OTHER PUBLICATIONS

Wilson et al. (Overview of the Preparation, Use and Biological Studies on Polyglycerol Polyricinoleate (PGPR). Food and Chemical Toxicology. 1998, 36, 711-718).*
Machine translated English equivalent of JP 05049398 A.*
Machine translated English equivalent of JP 06220484 A, Aug. 1994, pp. 1-6.*
Derwent Abstract of JP 06220484 A, Accession No. 1994-291195, Aug. 1994, 2 pages.*

* cited by examiner

*Primary Examiner* — Milton I Cano
*Assistant Examiner* — Brieann R Fink
(74) *Attorney, Agent, or Firm* — McAndrews, Held & Malloy, Ltd.

(57) ABSTRACT

A process for manufacturing polymers of glycerin and hydroxyl fatty acids, for example, polyglycerol polyricinoleates, which mix a polyglycerol with a hydroxyl fatty acid directly to form a reaction mixture, and then heat the reaction mixture to a temperature sufficient to cause it to polymerize through an esterification mechanism until the reaction mixture reaches a desired acid value.

17 Claims, No Drawings

US 8,101,707 B2

PROCESS FOR THE DIRECT MANUFACTURE OF POLYGLYCEROL POLYRICINOLEATE

This application is a 35 U.S.C. 371 National Stage entry of PCT Application Serial No. PCT/US2006/032237 filed on Aug. 17, 2006, which claims the benefit of U.S. provisional patent application No. 60/712,376 filed on Aug. 30, 2005, which is hereby incorporated by reference herein.

FIELD OF THE MENTION

The presently described technology relates to a process for manufacturing polymers of glycerin and hydroxyl fatty acids, for example, polyglycerol polyricinoleates ("PGPR").

BACKGROUND OF THE INVENTION

It is known in the art that the esterification of condensed castor oil fatty acids with polyglycerol may result in a potentially powerful water-in-oil emulsifier that may be used by the food industry, for example, in tin-greasing emulsions and as an emulsifier with lecithin to produce chocolate covertures and block chocolate.

As an emulsifier, PGPR has a low hydrophilic-lipophilic balance ("HLB") value and finds utility in water in oil emulsions such as low fat table spreads because of this property. PGPR has been used in foods, drugs and cosmetics. For example, PGPR is an emulsifier approved in many countries for use as an additive for chocolate.

One of PGPR's desired physical behaviors is the physical separation of solids in a slurry. Therefore, additional applications of PGPR includes its use in paints, coal slurries and other high solids compositions that typically require reduction in low shear viscosity or reduction in yield value of pseudo-plastic materials.

PGPR has been reported in several scientific articles and patents. For example, U.S. Pat. Nos. 4,590,086 and 4,971,721 (both to Takahashi, et al.) describe processes utilizing PGPR for the production of water-in-oil-in-water emulsions for medicines, cosmetics, foods, etc. The disclosures of these two patents are incorporated herewith by reference in their entirety.

PGPR has been the subject of a previous submission to the Food and Drug Administration of the United States of America as a part of GRAS Notification, No. 0009, for use as a rheology modification agent in a molten chocolate mass. In GRAS Notification, No. 0009, PGPR is defined as an interesterified polymer of polyricinoleic acid and polyglycerol.

Polyricinoleic acid is a polymer that can be created by the self-condensation of a 12-hydroxy, 9-octadecenoic acid fraction of fatty acids obtained from castor oil. The condensation reaction is typically carried out by heating castor oil fatty acids to about 200° C., with or without catalyst, and removing water of reaction. Acceptable catalysts are those known in the art and include acids such as phosphoric acid, bases such as sodium hydroxide and lipase enzymes, all of which are currently used to interesterify food grade fats and oils.

Polyglycerol can be obtained either by the controlled polymerization of substituted propyl-1, 2-oxyrane, or through the direct condensation of glycerin under highly basic conditions.

Polyricinoleic acid and polyglycerol can then be interesterified through esterification mechanism to form PGPR.

A full description of PGPR is given in the Fiftieth Edition of the Food Chemical Codex (FCC), published by the Institute of Medicine. Specifications and analytical chemistry associated with PGPR as a food additive are provided for in this reference. The FCC monograph, "Polyglycerol Polyricinoleic Acid," is hereby incorporated by reference in its entirety. The key specifications of PGPR suitable as a food additive listed in the FCC are as follows:

| | |
|---|---|
| Acid Value: | Not greater than 6.0; |
| Hydroxyl Value: | Between 80 and 100; |
| Iodine Value: | Between 72 and 103; |
| Saponification Value: | Between 170 and 210; and |
| Refractive Index: | Between 1.463 and 1.467 @ 65° C. |

All of the specifications listed above with the exception of refractive index are weight average analysis and do not indicate specific structural characteristics of PGPR. Taken on the whole, however, these weight average related specifications do indicate correct chemical structure, but with limited accuracy. Refractive index, however, is directly indicative of final chemical structure; e.g., if the oligomer distribution of PGPR is not correct or distributed differently on the polyglycerol backbone, the refractive index measurement will not comply with the specifications as described above.

In summary, the conventional process for making PGPR, as described in the GRAS Notification No. 0009, generally includes the steps of (1) condensing glycerin to make a polyglycerol; (2) condensing ricinoleic acid to make a polyricinoleic acid; and (3) interesterifying the two polymers to make the final PGPR product.

One problem with this conventional process is that the step of polymerization of ricinoleic acid is complicated by the fact that there is a requirement to follow the refractive index of the mixture while polymerization of ricinoleic acid and/or interesterification of polyglycerol and polyricinoleic acid is under way and to stop the reaction when the key value is indicated by the analysis. The refractive index test is not easily established in a manufacturing facility because the instrument is delicate, requires precise calibration and requires a circulating temperature bath set to a particular temperature, e.g., 65° C. It is therefore difficult to run the refractive index test at the kettle, and this often requires that the instrument be used in a laboratory setting, usually in a quality control laboratory. If one uses refractive index as the guide, one needs to run samples to the laboratory, and place them in the laboratory queue. This is both time consuming and inconvenient. Moreover, the refractive index requires a high degree of technical training and precision.

The three-step conventional process also reduces efficiency of production and adds cost to the product. Therefore, there is a need for a more economical and simplified method for manufacturing PGPR.

Further, in the conventional process, there is a tendency to produce compositions of darker color. This is most likely due to the added processing steps of preparing two separate ingredients, each having its own cycle of heating and cooling, along with the additional handling associated with the manufacture of each ingredient. As a result, there is a need for a method that can produce noticeably lower color end product, such as a clear yellow liquid rather than an amber liquid.

BRIEF SUMMARY OF THE INVENTION

One object of the presently described technology is to develop a simpler and more economical method for manufacturing PGPR by simplifying the polymerization reaction of glycerin and rincinoleic acid and the interesterification reaction of polyglycerol and polyricinoleic acid. The present technology achieves this object by polymerizing a mixture of ricinoleic acid and polyglycerol directly without the need of polymerizing ricinoleic acid first before being mixed with polyglycerol.

It has been surprisingly found that polymerization of ricinoleic acid in the presence of polyglycerol can achieve a resultant PGPR product meeting at least one or more of the specifications for such a product as set forth in the FCC noted above. More importantly, it has been surprisingly found that the presently described technology can achieve a PGPR product having oligomer distribution as measured by the refractive index identical or similar to a PGPR product made by the conventional three-step process described above. Although the refractive index specification as listed in the FCC is a critical parameter, it has been surprisingly found that when making PGPR using the presently described process, the achievement of the refractive index specification does not need to be tested in process to determine whether a desired PGPR product has been achieved. Indeed, it has been found that the presently described process will produce a PGPR product meeting FCC specifications in a consistent manner once the desired acid value is achieved (e.g., an acid value meeting the FCC specification).

In one aspect, the presently described technology provides a method of preparing polymers of glycerin and hydroxyl fatty acids. According to this method, a polyglycerol of a pre-selected average molecular weight is combined with a hydroxyl fatty acid, and then heated to a temperature sufficient to cause the reaction mixture to polymerize through an esterification mechanism until the reaction mixture reaches a desired acid value. When making a food grade PGPR, the desired acid value is 6.0 or lower.

In another aspect of the presently described technology, there is provided a polymer of glycerin and a hydroxyl fatty acid produced by the method of the present technology, which may be further used as an emulsifier in a dispersion composition containing fine particles of a solid such as coco powder, colored pigments, coal, $TiO_2$, ZnO, etc.

One advantage of the presently described technology is that the technology can reduce or even eliminate the need for the separate step of polymerizing ricinoleic acid as required by the conventional method. The presently described process is significantly faster than manufacturing and then interesterifying the separate polymers. The kinetics of the condensation process is such that the time required for condensing ricinoleic acid or another hydroxyl fatty acid in the presence of the polyglycerin is equivalent to when the condensation process is conducted independently of the polyglycerin. The presently described process saves the time required to complete the interesterification process, because the interesterification process is completed "in situ" with the co-polymerization process. This results in a significant time savings because it saves the time to transfer the separate ingredients into a third process vessel and eliminates the separate heat up and cool down times associated with running the interesterfication process (in addition to the typical 4 to 6 hours required to ensure the interesterfication is complete).

Another advantage of the presently described technology is that it eliminates the need for in process testing of refractive index and can achieve this measure successfully when the acid value drops sufficiently to indicate completion of the process. When the conventional process is used, the only test acceptable to determine if the interesterfication is completed successfully is the refractive index test, which as stated earlier is both inconvenient and costly. The process of the presently described technology can be followed by an acid number (i.e., acid value) analysis, which can be carried out at the chemical product reactor facility by the operator—without the need to carry samples to the quality laboratory. This can further increase the production efficiency and reduce the production cost of PGPR, because a simple acid value test requires only a simple glass burette, a pre-made indicator solution, and pre-calibrated titrant to complete, and can be run at the kettle. The acid value test is quick and easy to perform.

BRIEF DESCRIPTION OF SEVERAL VIEWS OF THE DRAWINGS

[Not Applicable]

DETAILED DESCRIPTION OF THE INVENTION

While the presently described technology will be described in connection with one or more preferred embodiments, it will be understood by those skilled in the art that the technology is not limited to only those particular embodiments. To the contrary, the presently described technology includes all alternatives, modifications, and equivalents as may be included within the spirit and scope of the appended claims.

The presently described technology encompasses in one aspect a process to manufacture polymers of glycerin and hydroxyl fatty acids by combining polyglycerol of a pre-selected average molecular weight with a hydroxyl fatty acid to form a reaction mixture, heating the reaction mixture to a sufficient temperature to cause the reaction mixture to polymerize through an esterification mechanism, and then maintaining the temperature required for polymerization until the reaction mixture reaches a desired acid value.

The presently described process is unique in that it can avoid the separate step of polymerizing the hydroxyl fatty acids before mixing such polymerized acids with polyglycerol as required in conventional processing. The present process is also unique in that it uses acid value to indicate the completion of the process. For example, when ricinoleic acid is the hydroxyl fatty acid used in the present process, and when a food-grade PGPR meeting FCC specifications is the target product, one can stop heating and the reaction process when the acid value of the reactions mixture falls below about 6.0. It has been found that such a PGPR product also meets the other FCC specifications, including a refractive index between 1.463 and 1.467 at 65° C. The presently described process is therefore simpler, more economical, and allows for polymerization of the ricinoleic acid in situ to produce a desired polymer of glycerin and hydroxyl fatty acids, such as a PGPR that has the correct refractive index as set forth by the FCC as noted above.

A person of ordinary skill in the art will understand that the presently described technology is not limited to produce food-grade PGPR meeting FCC specifications as stated above. For example, the present technology can produce PGPR products with acid values greater than 6.0, such as about 6.5, about 7.0, about 8.0, or another value desired by the manufacturer; with hydroxyl values lower than 80 or greater than 100, such as about 75 or about 105; with iodine values lower than 72 or greater than 103, such as about 70 or about 105; with saponification values lower than 170 or greater than 210, such as about 165 or about 215; or with refractive index values lower than 1.463 or greater than 1.467 at 65° C., such as about 1.460 or about 1.470 at 65° C.

For another example, the present technology can be used to produce polymers of glycerin and hydroxyl fatty acids other than PGPR with totally different desired product specifications, and a person of ordinary skill in the art will understand how to use for example, the acid value of the reaction mixture, as an indication of the completion of the reaction process.

Polyglycerols of desired average molecular weights prepared by polymerizing glycerin in accordance with any method known in the art can be used in the process of the presently described technology. One such method is described in the GRAS Notification No. 0009, which is incorporated herein by reference in its entirety.

Preferably, the average molecular weight of the polyglycerol suitable for the presently described technology is between about 166 and about 2000, alternatively from about 166 to about 400, for example at about 276. Suitable polyglycerols are, in particular, those of the general formula:

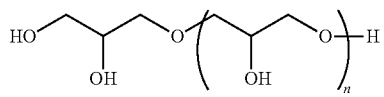

having an average degree of condensation n of from about 1 to about 11, preferably from about 2 to about 6, more preferably of from about 3 to about 6, and hydroxyl numbers of from approximately 1,350 to approximately 800, preferably from approximately 1,200 to approximately 900.

A person of ordinary skill in the art will understand how to pre-select average molecular weight of the polyglycerol for the presently described technology, recognizing that molecular weight of the polyglycerol is important for two reasons. First, it is important for proper control of the HLB of the final product. HLB in its simplest form is a direct measure of percent water solubility of an emulsifier, which multiplied by 5 gives the percent water solubility of the emulsifier in question. If the molecular weight of the polyglycerol is too high, the final HLB of the composition will be higher than required, and the composition will be too water soluble to give the correct performance in any predetermined emulsion system. On the other hand, if the polyglycerol molecular weight is too low, the HLB of the final composition will be lower than required and again this will not give the correct performance in any predetermined emulsion system because the water solubility will be too low. By defining the required hydroxyl value (i.e., hydroxyl numbers) of the polyglycerol, a person of ordinary skill in the art will be able to determine and pre-select the correct molecular weight needed. The second reason for specifically defining the molecular weight of the polyglycerol is because FCC defines a very specific homologue distribution for polyglycerol allowed in food products. This description can be found in the Fifth Edition of the FCC as referenced above and is incorporated herein by reference.

Technical-grade polyglycerol mixtures can be obtained, for example, by alkali-catalyzed condensation of glycerol at elevated temperatures typically in the range of from about 230° C. to about 270° C. Fractions having the desired degree of condensation and desired average molecular weight can optionally be obtained from the foregoing polyglycerol mixtures by distillation processes known in the art. Polyglycerols, which are obtained by another route, for example, from epichlorohydrin or glycidol, are also suitable for use in accordance with the presently described technology. The hydroxyl fatty acids used in the presently described technology can be any hydroxyl fatty acid suitable to be combined with polyglycerol to make an emulsifier. Such fatty acids can be obtained from castor oil or lesquerella oil, for example. Liquid fatty acids containing 18 to 22 carbon atoms are particularly suitable. Examples of suitable hydroxyl acids include, but are not limited to, ricinoleic acid (9c-18:1), isoricinoleic acid (12c-12:1), densipolic acid (9c,15c-18:2), lesquerolic acid (11c-20:1), and auricolic acid (11c, 17c-20:2), along with their hydrogenated counter parts: hydroxy stearic acid and hydroxy arachidic acid.

In accordance with at least one embodiment of the presently described technology, the polymer made from glycerin and hydroxyl fatty acids is a polyglycerol polyricinoleate (PGPR). PGPR can be represented by the following formula (I):

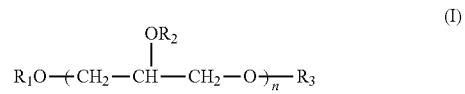

wherein n represents a number of from about 2 to about 12 and $R_1$, $R_2$ and $R_3$ each represents a hydrogen atom or a polyricinoleic acid of the following formula (II):

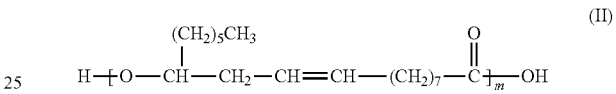

which m represents a number of from about 2 to about 10.

Further, in accordance with at least one embodiment of the presently described technology, the temperature required for polymerization can be in the range of from about 160° C. to about 240° C., more preferably at about 200° C.

The addition of a catalyst is not explicitly necessary for the practice of the presently described technology. However, a catalyst suitable for an esterification reaction can be added to the reaction mixture to enhance the rate of polymerization. Suitable basic catalysts include, for example, alkali metal or alkaline earth metal oxides or hydroxides, such as sodium hydroxide, potassium hydroxide, calcium hydroxide, alcoholates, and combinations thereof. Amines, especially strong amines such as guanadine carbonate and arginine, can also be used as basic catalysts for the presently described technology. Suitable acid catalysts include, for example, sulfonic acids, phosphoric acid, phosphorous acid, Lewis acids, such as tin salts, and combinations thereof.

One can also use a lipase enzyme, optionally a lipase enzyme approved for use in food applications, as the catalyst for use in the performance of the presently described technology. When a lipase enzyme is used as a catalyst, in accordance with another embodiment of the presently described technology, the temperature of reaction in the presence of the natural enzymatic catalyst required for polymerization is preferably in the range of from about 60 to about 80° C., more preferably at about 75° C. The mixture is preferably kept at a reduced pressure to facilitate removal of water of reaction.

In accordance with yet a further embodiment of the presently described technology there is provided a vacuum that can be applied to the reaction mixture to enhance the rate of the polymerization reaction. A preferred setting could include, for example, vacuum set to between 15 and 25 inches of mercury, and most preferably at about 20 inches of mercury for the total atmospheric pressure.

The polymers of glycerin and hydroxyl fatty acids produced according to the presently described technology are suitable for stabilization of aqueous emulsions and dispersions, and can be used to aid in the dispersion of fine particles, reduce viscosity at low shear values, and reduce the yield value of pseudo-plastic materials. Polymers of the presently described technology are particularly suitable for dispersions of solid particles because of their ability to effectively disperse and stabilize dispersions and reduce the yield value of high solid disperse systems. Examples of solid particles to be dispersed with aid of the polymers of glycerin and hydroxyl fatty acids of the presently described technology include, but are not limited to coco powder, colored pigments, coal, titanium dioxide ($TiO_2$), zinc oxide (ZnO), etc.

The polymers of glycerin and hydroxyl fatty acids of the presently described technology can also be used, for example, as emulsifiers for the preparation of cosmetic or pharmaceutical formulations, such as lotions, creams, personal sunscreens, colored cosmetics, and ointments.

Formulations that can benefit from the technology include, for example, color cosmetic compositions, chocolate and specifically enrobing chocolate formulations, coal slurries, and inorganic sunscreen formulations that incorporate titanium dioxide or zinc oxide as their active ingredients. Complex emulsions, such as margarines which rely on a combination of emulsifier and crystallized solid particles to achieve emulsion stability, can also benefit from incorporating small amounts of materials prepared by the present technology. Not to be limited by any particular theory, it is believed that the forces achieving particle stabilization in a solid dispersion and reducing low shear viscosity (yield value) can contribute to maintain a degree of particle separation across liquid droplet interfaces in complex emulsions, which is believed to contribute directly to stability between immiscible liquids in such emulsion systems.

The presently described technology and its advantages will be better understood by reference to the following examples. These examples are provided to describe specific embodiments of the present technology. By providing these specific examples, the inventor does not limit the scope and spirit of the present technology. It will be understood by those skilled in the art that the full scope of the presently described technology encompasses the subject matter defined by the claims appending this specification, and any equivalents of them.

EXAMPLES

Example 1

PGPR was prepared by reacting a mixture of 40 grams polyglycerol-3; 458 grams ricinoleic acid (castor oil fatty acids); 1 gram NaOH (50% in water); and 1 gram $Ca(OH)_2$ in a 1000 ml, four neck, round bottom flask. The flask was fitted with stirrer, $N_2$ sweep, a Dean-Stark trap and heating mantel. This mixture was heated to 200° C., and the temperature was maintained. Samples were taken from the flask every hour and measured for acid value by titration with potassium hydroxide. When the acid value reached 6.0, the heat was removed and the reaction was allowed to stop. During the entire reaction time, water was removed from the reaction mixture. The reaction product was analyzed and its analysis is shown below. A person skilled in the art will understand that this analysis is in compliance with the specification as set forth above and found in the Fifth Edition of the FCC.

| Analysis: | |
|---|---|
| Acid Value | 5.3 |
| Hydroxyl Value | 90 |
| Iodine Value | 87 |
| Saponification Value | 178 |
| Refractive Index | 1.4641 @ 65° C. |

Example 2

In this example, PGPR was prepared by reacting a mixture of 33.6 grams polyglycerol-3; and 366.4 grams ricinoleic acid (castor oil fatty acids) in a 500 ml, four neck, round bottom flask. The flask was fitted with stirrer, $N_2$ sweep, a Dean-Stark trap and heating mantel. This mixture was heated to 200° C., and the temperature was maintained. Samples were taken from the flask every hour and measured for acid value by titration with potassium hydroxide. When the acid value reached 6.0, the heat was removed and the reaction was allowed to stop. During the entire reaction time, water was removed from the reaction mixture. The reaction product was analyzed and its analysis is shown below. A person skilled in the art will understand that this analysis is in compliance with the specification as set forth above and found in the Fifth Edition of the FCC.

| Analysis: | |
|---|---|
| Acid Value | 3.3 |
| Hydroxyl Value | 87 |
| Iodine Value | 86 |
| Saponification Value | 182 |
| Refractive Index | 1.4652 @ 65° C. |

The above example shows that the process of the presently described technology to manufacture PGPR does not require a catalyst. Simply combining polyglycerol-3 with ricinoleic acid and heating to 200° C. with removal of water of reaction will produce a PGPR product having satisfactory results in terms of at least one of the FCC specification values noted above.

The present technology is now described in such full, clear, concise and exact terms as to enable any person skilled in the art to which it pertains, to practice the same. It is to be understood that the foregoing describes preferred embodiments of the invention and that modifications may be made therein without departing from the spirit or scope of the present technology as set forth in the appended claims.

The presently described technology may be claimed as:

1. A method of directly preparing polymers of poly(glycerol)-poly(ricinoleate), comprising the steps of:
    combining a poly(glycerol) with a non-polymerized ricinoleic acid, at a ratio of about 1:11 (w/w) to form a reaction mixture;
    condensing the non-polymerized ricinoleic acid in the reaction mixture while removing water to form polyricinoleate, and, contemporaneously with the condensation reaction, co-polymerizing and interesterifying the polyglycerol in the reaction mixture and the polyricinoleate until the reaction mixture reaches a desired acid value and a hydroxyl value of between about 80 and 100.

2. The method of claim 1, wherein the average molecular weight of the polyglycerol is between about 166 and about 2000.

3. The method of claim 1, wherein the average molecular weight of the polyglycerol is between about 166 to about 400.

4. The method of claim 1, wherein the step of condensation and contemporaneous co-polymerization and interesterification is conducted at a temperature in the range of from about 160° C. to about 240° C.

5. The method of claim 4, wherein the temperature is about 200° C.

6. The method of claim 1, further comprising the step of adding a catalyst to the mixture.

7. The method of claim 6, wherein the catalyst is a basic catalyst.

8. The method of claim 7, wherein the basic catalyst is a sodium hydroxide, a potassium hydroxide, a calcium hydroxide, a guanidine, an arginine or a combination thereof.

9. The method of claim 6, wherein the catalyst is an acid catalyst.

10. The method of claim 9, wherein the acid catalyst is a phosphoric or phosphorous acid or a combination thereof.

11. The method of claim 6, wherein the catalyst is a lipase enzyme.

12. The method of claim 11, wherein the lipase enzyme is a lipase enzyme approved for use in food applications.

13. The method of claim 11, wherein the step of condensation and contemporaneous co-polymerization and interestification is conducted at a temperature in the range of from about 60° C. to about 80° C.

14. The method of claim 1, further comprising the step of applying vacuum to the mixture to enhance the rate of water removal.

15. The method of claim 1, wherein the desired acid value is 6.0 or lower.

16. The method of claim 1, wherein the initial hydroxyl value of the non-reacted poly-glycerol is between about 800-1350.

17. A method of preparing polymers of poly(glycerol)-poly(ricinoleate), comprising the steps of:
   a. combining non-polymerized ricinoleic acid with poly(glycerol) having an initial hydroxyl value of between about 800 and 1350, at a ratio of about 11:1 (w/w) to form a reaction mixture;
   b. contemporaneously condensing the non-polymerized ricinoleic acid in the reaction mixture to form polyricinoleate and co-polymerizing the polyricinoleate with the polyglycerol in the reaction mixture while continuously removing water; and
   c. maintaining the condensation and co-polymerization reactions, until the reaction mixture reaches:
      i. a hydroxyl value of between 80 and 100;
      ii. a saponification value of between 170 and 210;
      iii. Iodine value of between 72 and 103; and
      iv. Refractive Index of between 1.463 and 1.467 at 65° C.

* * * * *